US012691195B2

(12) United States Patent
Bures

(10) Patent No.: US 12,691,195 B2
(45) Date of Patent: Jul. 28, 2026

(54) TRAY SANITIZATION SYSTEMS AND METHODS

(71) Applicant: SMITHS DETECTION INC., Edgewood, MD (US)

(72) Inventor: Brian Lee Bures, Bel Air, MD (US)

(73) Assignee: SMITHS DETECTION INC., Edgewood, MD (US)

( * ) Notice: Subject to any disclaimer, the term of this patent is extended or adjusted under 35 U.S.C. 154(b) by 513 days.

(21) Appl. No.: 17/926,778

(22) PCT Filed: May 21, 2021

(86) PCT No.: PCT/US2021/033607
§ 371 (c)(1),
(2) Date: Nov. 21, 2022

(87) PCT Pub. No.: WO2021/237062
PCT Pub. Date: Nov. 25, 2021

(65) Prior Publication Data
US 2023/0201399 A1      Jun. 29, 2023

Related U.S. Application Data

(60) Provisional application No. 63/028,740, filed on May 22, 2020.

(51) Int. Cl.
*A61L 2/26* (2006.01)
*A61L 2/10* (2006.01)
*A61L 2/14* (2006.01)

(52) U.S. Cl.
CPC ................... *A61L 2/26* (2013.01); *A61L 2/10* (2013.01); *A61L 2/14* (2013.01); *A61L*

*2202/11* (2013.01); *A61L 2202/123* (2013.01); *A61L 2202/14* (2013.01)

(58) Field of Classification Search
CPC ................. A61L 2/10; A61L 2/26; A61L 2/14
See application file for complete search history.

(56) References Cited

U.S. PATENT DOCUMENTS

| | | | |
|---|---|---|---|
| 5,067,192 A | 11/1991 | Guelfi et al. | |
| 6,655,577 B2 | 12/2003 | Mihaylov et al. | |
| 2008/0289649 A1 | 11/2008 | Woytkiw | |
| 2009/0252646 A1 | 10/2009 | Holden et al. | |
| 2014/0156561 A1 | 6/2014 | Steele et al. | |

(Continued)

FOREIGN PATENT DOCUMENTS

| | | |
|---|---|---|
| CN | 204637044 U | 9/2015 |
| CN | 109174766 A | 1/2019 |

(Continued)

OTHER PUBLICATIONS

European Extended Search Report, Application No. 21807876.4, dated Jul. 23, 2024, 12 pps.

(Continued)

*Primary Examiner* — Sean E Conley
(74) *Attorney, Agent, or Firm* — Armstrong Teasdale LLP

(57) ABSTRACT

Described herein is a tray sanitization assembly including a tray sanitization source positioned within a tray return system and configured to sanitize a baggage handling tray conveyed therethrough. Also described is a tray return system including a conveyor assembly including a conveyor for translating a baggage handling tray in a tray transfer direction, and the tray sanitization assembly.

15 Claims, 5 Drawing Sheets

(56) References Cited

U.S. PATENT DOCUMENTS

| | | |
|---|---|---|
| 2014/0158910 A1 | 6/2014 | Fletcher |
| 2016/0151530 A1 | 6/2016 | Kawanabe et al. |
| 2020/0324005 A1 | 10/2020 | Frazier |
| 2021/0330848 A1 | 10/2021 | Zhang et al. |

FOREIGN PATENT DOCUMENTS

| | | |
|---|---|---|
| CN | 109619362 A | 4/2019 |
| CN | 209236953 U | 8/2019 |
| CN | 209783208 U | 12/2019 |
| CN | 210320774 U | 4/2020 |
| CN | 111632161 A | 9/2020 |
| CN | 111939297 A | 11/2020 |
| CN | 112245638 A | 1/2021 |
| EP | 1588720 A1 | 10/2005 |
| EP | 2705858 A1 | 3/2014 |
| EP | 3878477 A1 | 9/2021 |
| EP | 3900746 A1 | 10/2021 |
| NO | 20181390 A1 | 6/2019 |
| WO | 2012122641 A1 | 9/2012 |
| WO | 2020070339 A1 | 4/2020 |
| WO | 2020086008 A1 | 4/2020 |
| WO | 2021097380 A1 | 5/2021 |
| WO | 2021212237 A1 | 10/2021 |

OTHER PUBLICATIONS

PCT International Search Report and Written Opinion, Application No. PCT/US2021/033607, dated Aug. 20, 2021, 10 pages.

Niina Ikonen et al., "Deposition of respiratory virus pathogens on frequently touched surfaces at airports", BMC Infectious Diseases, Aug. 29, 2018, 7 pages.

European Examination Report, Application No. 21807876.4, dated Jun. 13, 2025, 7 pages.

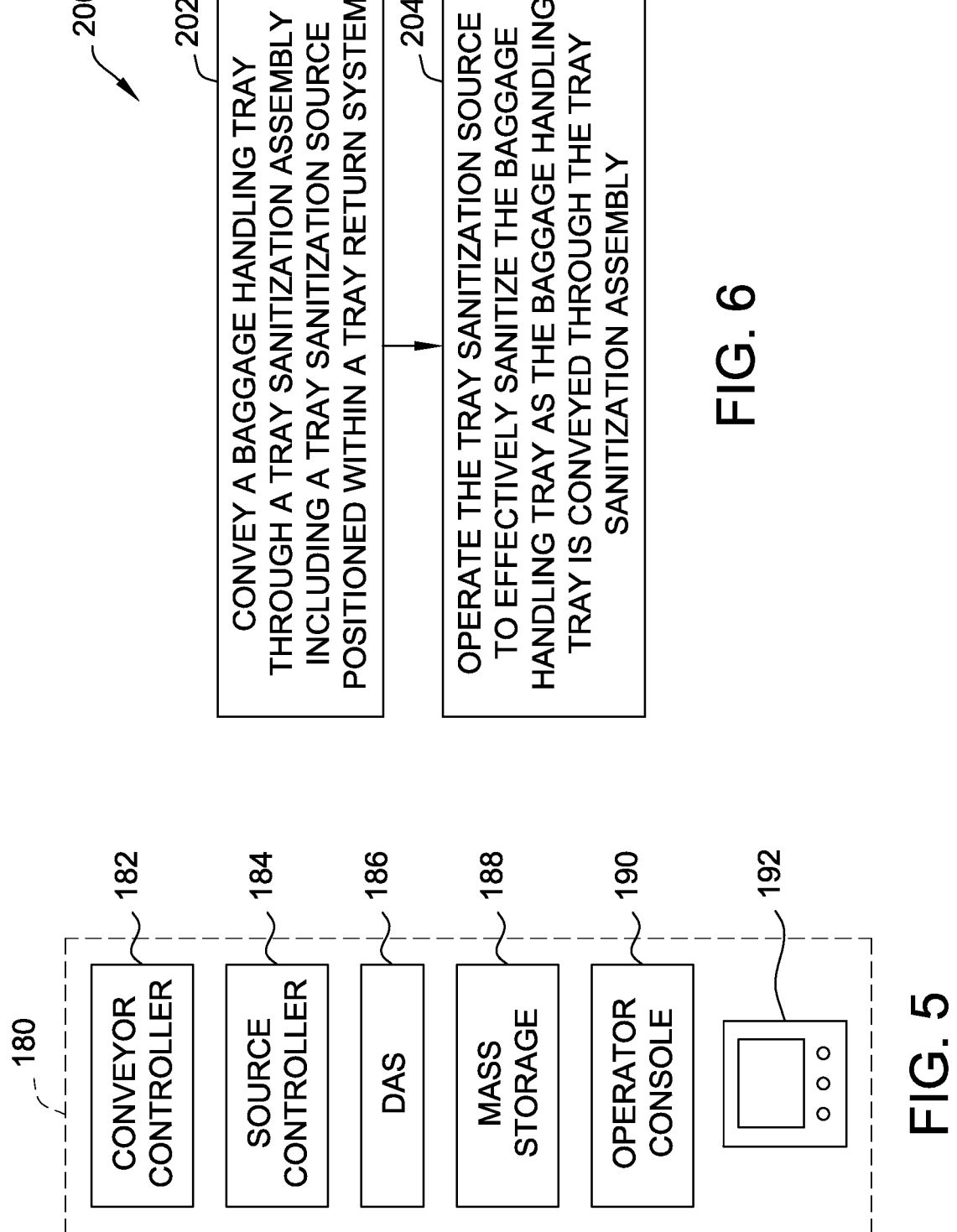

200

202
CONVEY A BAGGAGE HANDLING TRAY THROUGH A TRAY SANITIZATION ASSEMBLY INCLUDING A TRAY SANITIZATION SOURCE POSITIONED WITHIN A TRAY RETURN SYSTEM

204
OPERATE THE TRAY SANITIZATION SOURCE TO EFFECTIVELY SANITIZE THE BAGGAGE HANDLING TRAY AS THE BAGGAGE HANDLING TRAY IS CONVEYED THROUGH THE TRAY SANITIZATION ASSEMBLY

182 CONVEYOR CONTROLLER

184 SOURCE CONTROLLER

186 DAS

188 MASS STORAGE

190 OPERATOR CONSOLE

TRAY SANITIZATION SYSTEMS AND METHODS

CROSS-REFERENCE TO RELATED APPLICATIONS

This application claims the benefit of priority to U.S. Provisional Patent Application No. 63/028,740, filed May 22, 2020, the entire contents and disclosure of which are hereby incorporated by reference herein.

BACKGROUND

The embodiments described herein relate generally to baggage handling and checkpoint tray systems and methods and, more particularly, to systems and methods for sanitizing baggage handling and checkpoint trays, for example, in a tray return conveyor.

Recent studies show that trays in airports are a source of bacteria, germs, and viruses that can make travelers sick and lead to planes being quarantined. Travelers passing through security checkpoints are generally required to place some articles of clothing (e.g., jackets, shoes, belts), certain items from carry-on luggage (e.g., electronics, keys), and small carry-on items or luggage in trays, for security screening purposes. With multiple passengers using the trays, biological contaminants can be passed from personal items to the trays, and, subsequently, from the trays to other passengers' items.

Manual cleaning of the baggage handling trays is time consuming and conventionally involves the use of chemicals, which can increase operating costs. Additionally, antimicrobial surface coatings may not address all types of contaminants that may be present in the tray.

Accordingly, there is a need for a more efficient and cost-effective tray sanitization system.

BRIEF DESCRIPTION

In one aspect, a tray sanitization assembly is provided. The tray sanitization assembly includes a tray sanitization source positioned within a tray return system and configured to sanitize a baggage handling tray conveyed therethrough.

In another aspect, a tray return system including a conveyor assembly and a tray sanitization assembly is provided. The conveyor assembly includes a conveyor for translating a baggage handling tray in a tray transfer direction. The tray sanitization assembly includes a tray sanitization source positioned within the tray return system and configured to effectively sanitize the tray as the tray is conveyed by the conveyor.

In a further aspect, a method for sanitizing baggage handling trays is provided. The method includes conveying a baggage handling tray through a tray sanitization assembly including a tray sanitization source positioned within a tray return system, and operating the tray sanitization source to effectively sanitize the baggage handling tray as the baggage handling tray is conveyed through the tray sanitization assembly

BRIEF DESCRIPTION OF THE DRAWINGS

FIG. 5 is a schematic diagram of an exemplary control system for use in the tray sanitization systems shown in FIGS. 1-4.

FIG. 6 is a flow diagram of a method for sanitizing baggage handling trays using a tray sanitization system implemented as part of a tray return system.

DETAILED DESCRIPTION

The present disclosure provides systems and methods for effectively and efficiently sanitizing baggage handling trays. The trays are exposed to a sanitization source that effectively sanitizes the trays. In the exemplary embodiment, the tray sanitization systems of the present disclosure are implemented as part of a tray return system.

Tray return systems are used in some airports to automate the return of used trays to passengers awaiting passage through a security checkpoint, from a location beyond the security checkpoint. In at least some cases, the tray return systems include a conveyor assembly, such as a belt or system of rollers, that convey the tray between locations for subsequent use thereof. The present disclosure contemplates incorporating tray sanitization systems and methods into such a tray return system, to more efficiently use the time during which the tray is being conveyed for subsequent use, and to enable tray sanitization between uses of the tray without significantly adding to a tray "downtime", or time during which a tray is not in use or available for use. Accordingly, as described further herein, the tray sanitization systems are configured to effectively sanitize the baggage handling trays without significantly slowing the speed of the tray return systems. In particular, the trays are exposed to a sanitization source for a sufficient amount of time (e.g., one or more seconds) to effectively sanitize the trays without slowing the speed of the tray return.

The systems and methods described herein also facilitate the sanitization of baggage handling trays without requiring consumables, such as liquid chemicals, which facilitates reducing costs and labor associated with tray sanitization.

As used herein, "sanitization" or "effective sanitization" refers to a removal or inactivation of at least a portion of biological contaminants on a surface, such as removal or inactivation of at least 90% of biological contaminants on the surface, or at least 95% of biological contaminants on the surface, or at least 99% of biological contaminants on the surface, or at least 99.9% of biological contaminants on the surface.

Figure 1:
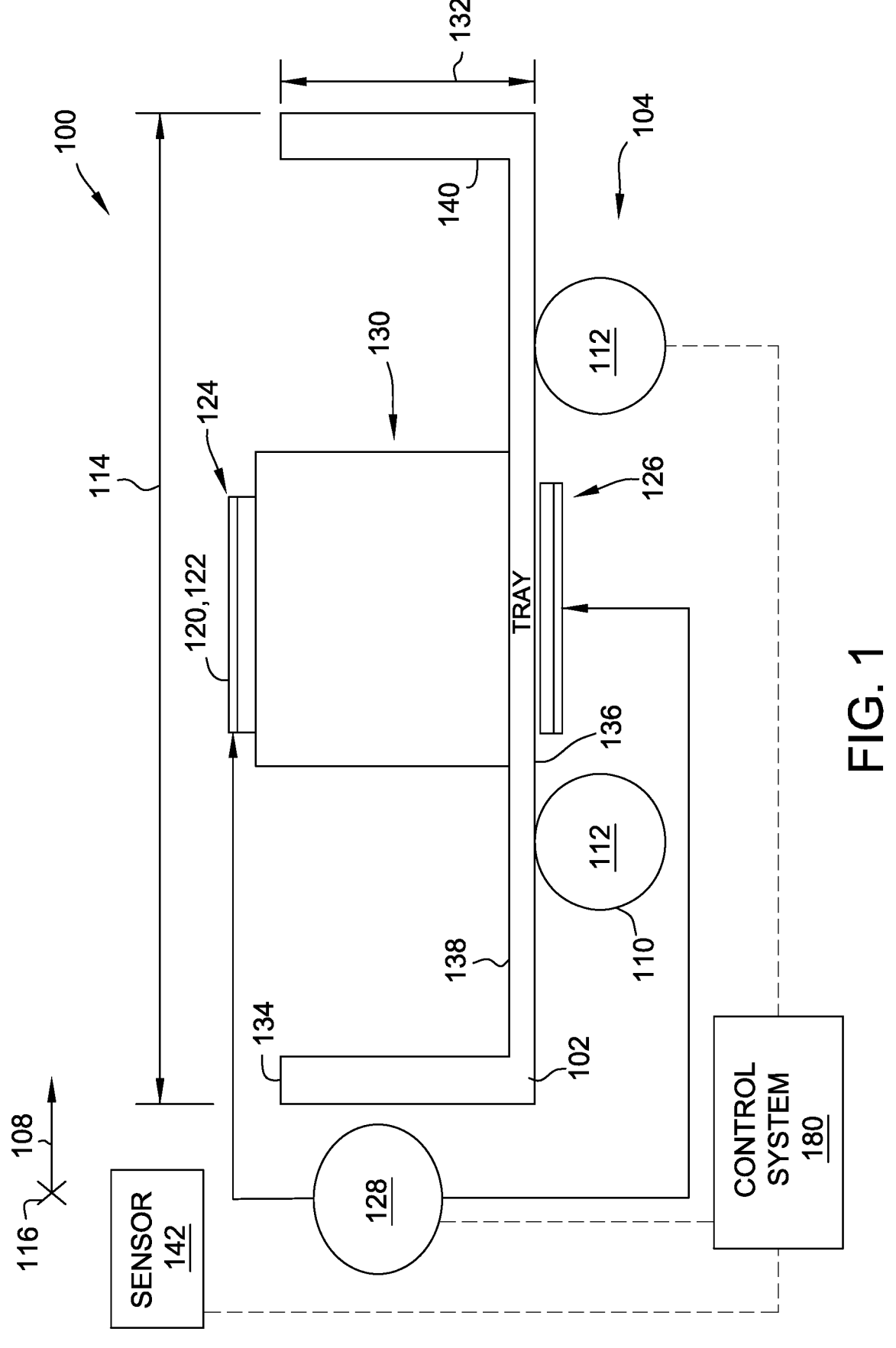
FIG. 1 is a schematic diagram of an exemplary tray sanitization system implemented as part of a tray return system and including a direct plasma discharge sanitization source.

Turning now to the figures, FIG. 1 is a perspective view of a tray return system 100 for returning a baggage handling or checkpoint tray 102 from a first location (e.g., a location beyond a security checkpoint in an airport) to a second location (e.g., a location before the security checkpoint). System 100 generally includes a conveyor assembly 104 and a tray sanitization assembly or sub-system 106 (also referred to more generally as a tray sanitization system).

In the exemplary embodiment, conveyor assembly 104 is configured to translate trays 102 along a tray transfer direction 108. Conveyor assembly 104 includes one or more conveyors 110, embodied in FIG. 1 as one or more sets of rollers 112. Rollers 112 may be spaced apart along tray transfer direction 108 by a distance less than a length 114 of trays 102.

In some embodiments, conveyor 110 includes only one set of rollers 112, and rollers 112 have a length (not shown) that extends in a lateral direction 116 (i.e., perpendicular to tray transfer direction 108) and that is greater than or equal to a width (not shown) of trays 102. That is, each roller 112 is disposed beneath a full width of tray 102. In other embodiments, conveyor 110 includes two parallel sets of rollers 112, each set of rollers 112 positioned to correspond to and support one lateral edge of tray 102 as tray 102 is conveyed by conveyor 110. Conveyor(s) 110 may include any additional or alternative components, such as belts, rails, chains, and the like. Conveyor 110 translates tray 102 through tray return system 100 at any suitable speed, such as up to 0.2 m/s or up to 0.5 m/s.

Tray sanitization assembly 106 includes at least one sanitization source 120. In the embodiment shown in FIG. 1, sanitization source 120 includes a plasma discharge source 122, specifically a direct plasma discharge source. Plasma discharge source 122 includes two electrodes 124, 126 spaced from one another and coupled to a power source 128, specifically a high voltage power source 128. In the exemplary embodiment, power source 128 operates at frequencies between 1 kHz and 100 MHz and voltages between 10 kV and 100 kV to generate plasma discharge (generally shown at 130) between electrodes 124, 126. Discharge 130 may be a barrier (capacitive or resistive) discharge or RF frequency barrier-less discharge. Tray 102 is conveyed by conveyor(s) 110 through plasma discharge 130 to sanitize tray 102. Specifically, discharge 130 inactivates biological contaminants present on the outer surface of tray 102 as discharge 130 contacts the surface of tray 102.

In the illustrated embodiment, electrodes 124, 126 are spaced apart by a distance approximately equal to a depth or height 132 of tray 102. A first electrode 124 is positioned above a top edge 134 of tray 102, such that electrode 124 and tray 102 do not contact one another as tray 102 passes beneath electrode 124. Electrode 124 may be coupled to a ceiling surface (not shown) of tray return system 100. A second electrode 126 is positioned below a bottom surface 136 of tray 102, such that electrode 126 and tray 102 do not contact one another as tray 102 passes above electrode 126. Electrode 126 may be positioned between longitudinally adjacent rollers 112 and/or between parallel sets of laterally spaced rollers 112.

Although electrodes 124, 126 are illustrated as parallel electrodes, electrodes 124, 126 may be oriented other than parallel in any alternative embodiment, such as point to plane, edge to plane, or any other suitable orientation that enables plasma discharge therebetween. The relative orientation of electrodes 124, 126 may be adjusted or selected for optimal sanitization or sterilization of tray 102.

In this embodiment, discharge 130 contacts both bottom surface 136 and a top outer surface 138 of tray 102 and sanitizes these surfaces 136, 138. At least a portion of side surfaces 140 of tray 102 may also be contacted by discharge 130. Accordingly, a majority of an overall outer surface of tray 102 is sanitized by discharge 130.

Electrodes 124, 126 may be covered in a dielectric or resistive material to prevent high currents and arcing, which can be damaging. In some embodiments, sanitization source

120 (e.g., plasma discharge source 122) may include one or more additional electrode pairs, such as two electrodes respectively positioned on opposing lateral sides of conveyor 110, to sanitize lateral side surfaces (not shown) of tray 102. Additionally or alternatively, electrodes 124, 126 may be implemented as multiple pairs of electrodes (e.g., an array of top electrodes and an array of bottom electrodes).

The level of sanitization of tray 102 by plasma discharge source 122 (e.g., a direct plasma discharge source) may depend upon, for example, operating parameters of power source 128 (e.g., frequency, voltage, etc.), characteristics of the resulting discharge 130 (e.g., intensity), the speed of conveyor 110, the size of electrodes 124, 126, and/or the distance between electrodes 124, 126 (e.g., the size of trays 102).

In the illustrated embodiment, tray return system 100 also includes one or more sensors 142, such as light- and/or motion-based sensors, associated with tray sanitization assembly 106. Sensors 142 are configured to sense the presence of tray 102 on conveyor 110 in a location upstream of tray sanitization assembly 106—specifically, upstream of tray sanitization source 120. When tray 102 is sensed, tray sanitization assembly 106 may be activated, for example, by activating power supply 128. In this way, power consumption by tray sanitization assembly 106 may be reduced. Tray sanitization assembly 106 may be deactivated (e.g., by deactivating power supply 128) when sensor 142 has not sensed an incoming tray 102 for a predefined period of time (e.g., one or more seconds). Additionally or alternatively, another sensor (not shown) downstream of tray sanitization assembly 106 may detect when tray 102 has reached a location beyond tray sanitization assembly 106 and, therefore, if no further trays 102 are detected by sensor 142, tray sanitization assembly 106 may be deactivated.

Figure 2:
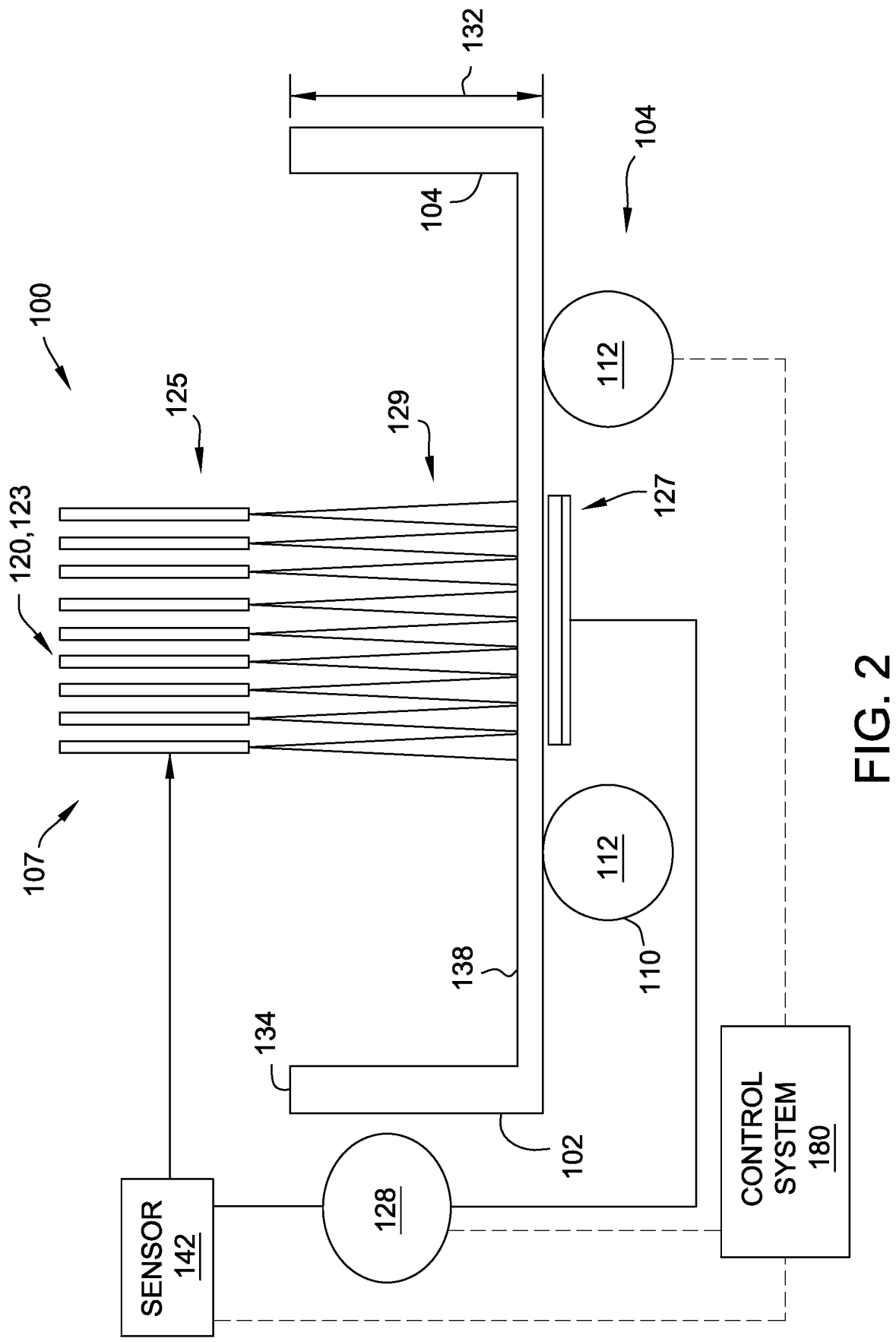
FIG. 2 is a schematic diagram of another exemplary tray sanitization system implemented as part of a tray return system and including a direct plasma discharge sanitization source.

Another embodiment of tray return system 100 including an alternative tray sanitization assembly 107 is shown in FIG. 2. In this embodiment, sanitization source 120 also includes a plasma discharge source 123, specifically a direct plasma discharge source. Plasma discharge source 123 includes a plurality of electrodes, including an array of point or edge electrodes 125 (also referred to as top electrodes) and a plane electrode 127 (also referred to as a bottom electrode).

Top electrodes 125 and bottom electrodes 127 are coupled to high voltage power source 128, which energizes electrodes 125, 127 to generate a plurality of regions of plasma discharge 129 therebetween. Tray 102 is conveyed by conveyor(s) 110 through plasma discharge 129 to sanitize tray 102. Specifically, discharge 129 inactivates biological contaminants present on the outer surface of tray 102 as discharge 129 contacts the surface of tray 102.

Top electrodes 125 are arranged in an array and are evenly spaced from one another in this embodiment. Where top electrodes 125 are edge electrodes (as illustrated in FIG. 2, in which an edge of electrodes 125 faces or is directed towards bottom electrode 127), electrodes 125 may be parallel to one another. Top electrodes 125 are spaced from bottom electrode 127 by a distance approximately equal to height 132 of tray 102. Top electrodes 125 are positioned above top edge 134 of tray 102, such that top electrodes 125 and tray 102 do not contact one another as tray 102 passes beneath top electrodes 125. Top electrodes 125 may be coupled to a ceiling surface (not shown) of tray return system 100. Bottom electrode 127 is positioned below bottom surface 136 of tray 102, such that bottom electrode 127 and tray 102 do not contact one another as tray 102 passes above bottom electrode 127. Bottom electrode 127 may be positioned between longitudinally adjacent rollers 112 and/or between parallel sets of laterally spaced rollers 112.

In this embodiment, discharge 129 contacts both bottom surface 136 and top outer surface 138 of tray 102 and sanitizes these surfaces 136, 138. At least a portion of side surfaces 140 of tray 102 may also be contacted by discharge 129. Accordingly, a majority of an overall outer surface of tray 102 is sanitized by discharge 129.

Figure 3:
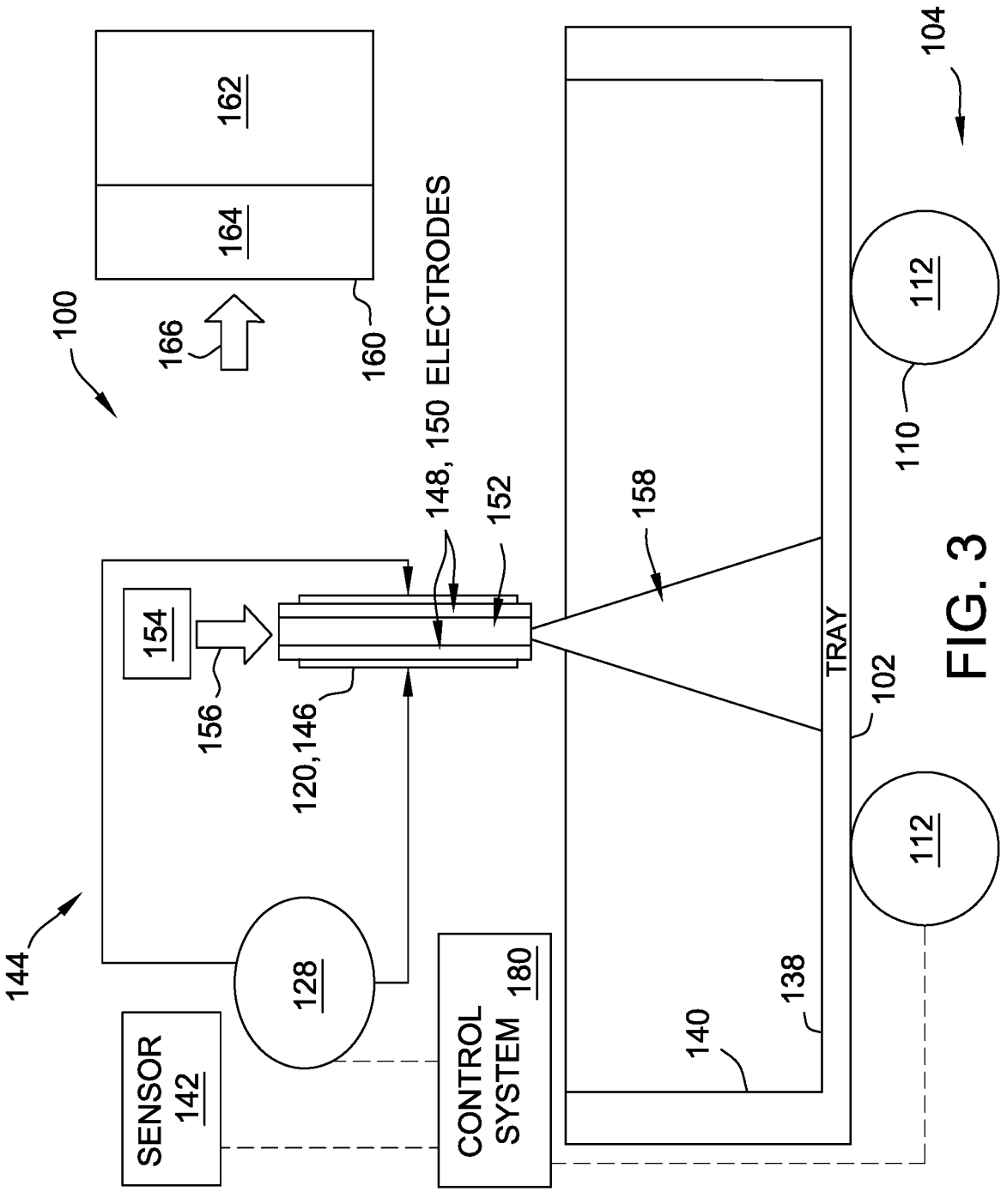
FIG. 3 is a schematic diagram of another exemplary tray sanitization system implemented as part of a tray return system and including an indirect plasma discharge or plasma jet sanitization source.

Another embodiment of tray return system 100 including an alternative tray sanitization assembly 144 is shown in FIG. 3. In this embodiment, sanitization source 120 includes a plasma discharge source 146. Notably, however, plasma discharge source 146, including a pair of electrodes 148, 150 generating a plasma discharge 152 therebetween, is an indirect plasma discharge source, also referred to as a plasma jet or torch. That is, discharge 152 does not directly contact tray 102.

Rather, tray sanitization assembly 144 further includes an airflow source 154, such as a fan, blower, pump, compressor, or the like. Airflow source 154 ejects a stream of air 156 therefrom and between electrodes 148, 150. Air 156 is activated by discharge 152 to produce a jet 158 of activated oxygen products (e.g., OH, hydrogen peroxide) and ozone. The (oxygen) activation products in jet 158 contact the outer surface of tray 102 to inactivate biological contaminants present on the outer surface of tray 102—that is, to sanitize tray 102.

Because discharge 152 does not need to directly contact tray 102, electrodes 148, 150 can be closer and/or smaller, as compared to electrodes 124, 126 shown in FIG. 1. Therefore, in at least some cases, tray sanitization assembly 144 may require less power to operate than tray sanitization assembly 106.

In the illustrated embodiment, indirect plasma discharge source 146 is fixedly positioned vertically above tray 102 transported using conveyor 110. In this embodiment, jet 158 contacts top outer surface 138 of tray 102. At least a portion of side surfaces 140 of tray 102 may also be contacted by jet 158. Tray sanitization assembly 144 may include any number of indirect plasma discharge sources 146 to effectively sanitize trays 102. For example, any number of indirect plasma discharge sources 146 (and corresponding airflow sources 154) in any orientation (e.g., to direct jets 158 of activation products at side and/or bottom surfaces of tray 102) may be used. Additionally or alternatively, plasma discharge source 146 and airflow source 154 may be mounted on a pivotable surface, such that plasma discharge source 146 and airflow source 154 may be moved (e.g., pivoted, rotated, etc.) to direct jet 158 across multiple surfaces of tray 102 as tray 102 is conveyed.

In the illustrated embodiment, tray sanitization assembly 144 further includes an air return sub-assembly 160 to filter the ozone products from tray return system 100. Air return subassembly 160 includes a flow control device 162 (e.g., a fan, pump, blower, and the like) and an air filter 164. Flow control device 162 controls the flow of air in tray return system 100, to direct air 166 through air filter 164 to filter ozone products from the flow of air 166. Air filter 164 may include a carbon filter or any other suitable ozone filter.

In some embodiments, airflow source 154 may be a source of gases other than air, such as helium or argon. In some such embodiments, air return system 160 may not be needed, as ozone or other potentially harmful activation products may not be produced.

The level of sanitization of tray 102 by jet 158 may depend upon, for example, speed and/or volume of stream of air 156, temperature and/or humidity conditions within tray return system 100, operating parameters of power source 128 (e.g., frequency, voltage, etc.), characteristics of the resulting discharge 152 (e.g., intensity), the speed of conveyor 110, the size of electrodes 148, 150, and/or the distance between electrodes 148, 150.

Figure 4:
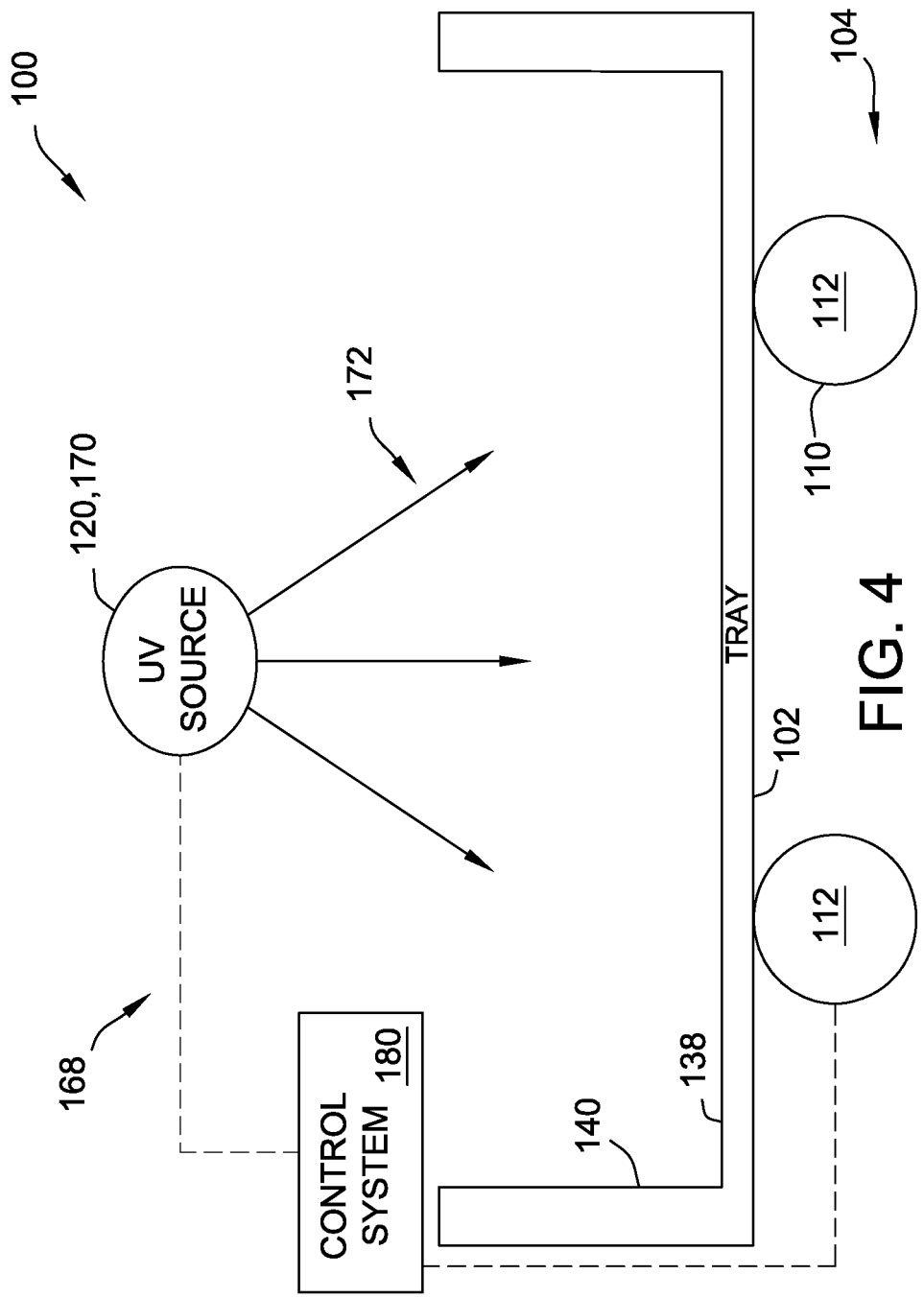
FIG. 4 is a schematic diagram of another exemplary tray sanitization system implemented as part of a tray return system and including an ultraviolet (UV) radiation sanitization source.

Another embodiment of tray return system 100 including an alternative tray sanitization assembly 168 is shown in FIG. 4. In this embodiment, sanitization source 120 includes an ultraviolet (UV) light source 170. UV light source 170 is positioned above tray 102 being translated on conveyor 110, and is configured to direct UV light rays (illustrated at 172) onto the outer surface of tray 102. The UV light rays interact with the surface of tray 102 to inactivate the biological contaminants thereon, in order to sanitize tray 102.

In the illustrated embodiment, UV light source 170 is fixedly positioned vertically above tray 102 transported using conveyor 110. In this embodiment, UV rays 172 contact top outer surface 138 of tray 102. At least a portion of side surfaces 140 of tray 102 may also be contacted by UV rays 172. Tray sanitization assembly 168 may include any number of UV light sources 170 to effectively sanitize trays 102. For example, any number of UV light sources 170 in any orientation (e.g., to direct UV rays 172 at side and/or bottom surfaces of tray 102) may be used. Additionally or alternatively, UV light source 170 may be mounted on a pivotable surface, such that UV lights source 170 may be moved (e.g., pivoted, rotated, etc.) to direct UV rays 172 across multiple surfaces of tray 102 as tray 102 is conveyed.

In some embodiments, UV light source 170 is continuously activated to continuously emit UV rays 172. In other embodiments, UV light source 170 may be activated and deactivated responsive to the detection of incoming trays 102 (e.g., using a sensor 142 as described above).

The level of sanitization of tray 102 by UV light rays 172 may depend upon, for example, operating parameters of UV light source 170 (e.g., wavelength, intensity), and the speed of conveyor 110 (e.g., duration of exposure of tray 102 to rays 172).

In any of the above-described embodiments, conveyor assembly 104 and tray sanitization assembly 106/107/144/168 are controlled by a control system 180. In one embodiment, as shown in FIG. 5, control system 180 includes a conveyor controller 182, a source controller 184, a data acquisition system (DAS) 186, a mass storage system 188, an operator console 190, and a display device 192.

Conveyor assembly 106 may be controlled by conveyor controller 182, which may define the speed and/or direction of conveyor(s) 110. Source controller 184 may control, in some embodiments, activation, deactivation, and/or operating parameters of power source 128. DAS 186 may receive and interpret sensor data from sensor(s) 142 to determine when to active and/or deactivate power source 128. Source controller 184 may control, in other embodiments, activation, deactivation, and/or operating parameters of UV light source 170.

Mass storage system 188 includes any suitable memory hardware, and stores any operating parameters or control instructions for any other component of control system 180, as well as any data received and/or used thereby. Operator console 190, which may include display device 192, enables an operator to view and/or modify any operating parameters or control instructions for any component of control system 180. Operator console 190 and/or display device 192 may include an input device, such as a mouse and/or a keyboard, to receive input from an operator.

In some embodiments, control system 180 is one system configured to perform the functions described herein. In other embodiments, control system 180 includes two or more separate systems, such as a first system that controls conveyor assembly 104, and a second system that controls power source 128 and/or UV light source 170.

Conveyor controller 182, source controller 184, DAS 186, and/or operator console 190 may include one or more processors (not specifically shown). As used herein, the term processor is not limited to only integrated circuits referred to in the art as a processor, but broadly refers to a computer, a microcontroller, a microcomputer, a programmable logic controller, an application specific integrated circuit and any other programmable circuit.

Control system 180 may include additional, fewer, and/or alternative components, including any suitable processing and/or computing component necessary to carry out the methods described herein. For example, control system 180 may: (i) convey a baggage handling tray through a tray sanitization assembly including a tray sanitization source positioned within a tray return system (e.g., by controlling a conveyor), and (ii) operate the tray sanitization source to effectively sanitize the baggage handling tray conveyed as the baggage handling tray is conveyed through the tray sanitization assembly.

FIG. 6 is a flow diagram of a method 200 of sanitizing a baggage handling tray (e.g., tray 102). Method 200 includes conveying 202 a baggage handling tray through a tray sanitization assembly (e.g., tray sanitation assembly 106/107/144/168) including a tray sanitization source (e.g., tray sanitization source 120) positioned within a tray return system (e.g., tray return system 100). Method 200 also includes operating 204 the tray sanitization source to effectively sanitize the baggage handling tray conveyed as the baggage handling tray is conveyed through the tray sanitization assembly.

The above-described systems and methods facilitate efficiently sanitizing baggage handling trays within a tray return. This arrangement enables reduced reliance on consumables (e.g., liquid chemicals) without increasing labor or time for effectively sanitizing the trays.

Although specific features of various embodiments of the disclosure may be shown in some drawings and not in others, this is for convenience only. In accordance with the principles of the disclosure, any feature of a drawing may be referenced and/or claimed in combination with any feature of any other drawing.

This written description uses examples to describe embodiments of the disclosure, including the best mode, and also to enable any person skilled in the art to practice the disclosure, including making and using any devices or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A tray sanitization assembly comprising:
a tray sanitization source positioned within a tray return system and configured to sanitize a baggage handling tray conveyed therethrough, wherein said tray sanitization source comprises a plasma discharge source comprising a pair of electrodes configured to generate plasma discharge therebetween.

2. The tray sanitization assembly of claim 1, wherein said plasma discharge source comprises a direct plasma discharge source configured to cause the plasma discharge to directly contact an outer surface of the tray to inactivate biological contaminants thereon.

3. The tray sanitization assembly of claim 2, wherein said pair of electrodes are spaced apart by a distance greater than a height of the tray.

4. The tray sanitization assembly of claim 1, wherein said plasma discharge source comprises an indirect plasma discharge source, said tray sanitization assembly further comprising an airflow source configured to direct a stream of air between said pair of electrodes to generate a jet of activation products configured to contact an outer surface of the tray to inactivate biological contaminants thereon.

5. The tray sanitization assembly of claim 4, further comprising an air return system comprising a flow control device and an air filter.

6. The tray sanitization assembly of claim 1, further comprising a sensor upstream of said tray sanitization source and configured to detect an incoming tray and selectively activate said tray sanitization source in response to detecting the incoming tray.

7. The tray sanitization assembly of claim 1, wherein said plasma discharge source comprising an array of point or edge electrodes spaced from a plane electrodes and configured to generate plasma discharge between said array of point or edge electrodes and said plane electrode, and wherein said plasma discharge source comprises a direct plasma discharge source configured to cause the plasma discharge to directly contact an outer surface of the tray to inactivate biological contaminants thereon.

8. A tray return system comprising:
a conveyor assembly comprising a conveyor for translating a baggage handling tray in a tray transfer direction; and
a tray sanitization assembly comprising a tray sanitization source positioned within the tray return system and configured to effectively sanitize the tray as the tray is conveyed by said conveyor, wherein the tray sanitization source comprises a plasma discharge source comprising a pair of electrodes configured to generate plasma discharge therebetween.

9. The tray return system of claim 8, wherein said conveyor comprises a plurality of rollers.

10. The tray return system of claim 9, wherein a first electrode of said pair of electrodes is positioned between adjacent rollers of said plurality of rollers and below a bottom surface of the tray.

11. The tray return system of claim 8, wherein said conveyor translates the tray in the tray transfer direction through said tray sanitization assembly at a speed up to 0.5 m/s.

12. The tray return system of claim 8, wherein said plasma discharge source comprises a direct plasma discharge source configured to cause the plasma discharge to directly contact an outer surface of the tray to inactivate biological contaminants thereon.

13. The tray return system of claim 8, wherein said plasma discharge source comprising an array of point or edge electrodes spaced from a plane electrodes and configured to generate plasma discharge between said array of point or edge electrodes and said plane electrode, and wherein said plasma discharge source comprises a direct plasma discharge source configured to cause the plasma discharge to directly contact an outer surface of the tray to inactivate biological contaminants thereon.

14. The tray return system of claim 8, wherein said plasma discharge source comprising a pair of electrodes configured to generate plasma discharge therebetween, and wherein said plasma discharge source comprises an indirect plasma discharge source, said tray sanitization assembly further comprising an airflow source configured to direct a stream of air between said pair of electrodes to generate a jet of activation products configured to contact an outer surface of the tray to inactivate biological contaminants thereon.

15. A method for sanitizing baggage handling trays, the method comprising:

conveying a baggage handling tray through a tray sanitization assembly including a tray sanitization source positioned within a tray return system; and operating the tray sanitization source to effectively sanitize the baggage handling tray as the baggage handling tray is conveyed through the tray sanitization assembly, wherein operating the tray sanitization source comprises operating one of:

(i) a direct plasma discharge source including a pair of electrodes configured to generate plasma discharge therebetween and to cause the plasma discharge to directly contact an outer surface of the tray to inactivate biological contaminants thereon, (ii) a direct plasma discharge source including an array of point or edge electrodes spaced from a plane electrodes and configured to generate plasma discharge between the array of point or edge electrodes and the plane electrode, the direct plasma discharge source further configured to cause the plasma discharge to directly contact an outer surface of the tray to inactivate biological contaminants thereon;

(iii) an indirect plasma discharge source including a pair of electrodes configured to generate plasma discharge therebetween, wherein an airflow source is configured to direct a stream of air between the pair of parallel electrodes to generate a jet of activation products configured to contact an outer surface of the tray to inactivate biological contaminants thereon, and (iv) an ultraviolet (UV) light source configured to emit UV light rays towards an outer surface of the tray to inactivate biological contaminants thereon.

* * * * *